United States Patent [19]
Yoshida

[11] Patent Number: 5,216,239
[45] Date of Patent: Jun. 1, 1993

[54] RESIDUAL FLUID DETECTION APPARATUS FOR DETECTING FLUID AT THE BOTTOM OF A BOTTLE USING BOTH IR AND VISIBLE LIGHT

[75] Inventor: Hajime Yoshida, Tokyo, Japan
[73] Assignee: Hajime Industries Ltd., Tokyo, Japan
[21] Appl. No.: 747,293
[22] Filed: Aug. 19, 1991
[51] Int. Cl.$^5$ ............................................. G01N 21/90
[52] U.S. Cl. ................................ 250/223 B; 356/240
[58] Field of Search ................. 250/223 B, 339, 341, 250/343, 349, 301; 356/240; 209/588, 582, 577, 524

[56] References Cited
U.S. PATENT DOCUMENTS

| 4,221,961 | 9/1980 | Payton | 250/223 B |
| 4,368,980 | 1/1983 | Aldred et al. | 209/582 |
| 4,551,627 | 11/1985 | Reich | 250/223 B |
| 4,682,023 | 7/1987 | Yoshida | 250/223 B |
| 4,943,713 | 7/1990 | Yoshida | 250/223 B |

*Primary Examiner*—David C. Nelms
*Assistant Examiner*—John R. Lee
*Attorney, Agent, or Firm*—Bauer & Schaffer

[57] ABSTRACT

A light source irradiates the bottom of a bottle with light that contains visible light rays and infrared rays. Two photoelectric conversion sensors remove the light passing through the bottle bottom from the light source. An optical filter which passes only infrared rays placed in front of the light receiving surface of one of the photoelectric conversion sensors, and the outputs from the two photoelectric conversion sensors are compared directly and a signal is provided when a difference between the outputs exceeds a predetermined value.

9 Claims, 7 Drawing Sheets

RESIDUAL FLUID DETECTION APPARATUS FOR DETECTING FLUID AT THE BOTTOM OF A BOTTLE USING BOTH IR AND VISIBLE LIGHT

BACKGROUND OF THE INVENTION

1. Field of the Invention

The present invention relates generally to detection apparatus and, more particularly, to a residual liquid detection apparatus which detects liquid such as the washing liquid or the like remaining at the bottom of bottles such as transparent bottles made of glass or the like.

2. Description of the Prior Art

Drinking water or beverages such as beer and the like are loaded into glass bottles for marketing. Such bottles pass through a washing process before filling the bottles with the liquid. Especially, recycled bottles such as beer bottle that are reused after use by the consumer require a thorough washing in view of mixtures of trash or waste often found inside the bottle. Washing is conducted with detergent liquid and clean water, and there are cases where such detergent mixed water remains in the bottle due to the incomplete rinsing. Needless to say, subsequent refill beverage is for human consumption, it is not desired that a residual waste liquid remain in the bottle prior to refilling.

As for the conventional residual liquid detection methods, there are methods that detect the residual liquid by the absorbance ratios of high frequency waves, supersonic waves, or infrared rays. In another method, residual liquid is detected by measuring the differences in the capacitance therefore a pair of electrodes. The present trend lies mainly with detection methods by the use of infrared rays.

However, when the volume of the residual liquid is large, residual liquid detection is relatively easy by any of the methods mentioned above. However, it is extremely difficult to detect very small volumes of residual liquid, although it is desired to have apparatus that will provide stable detection of very small volumes.

One reason that makes the detection of small volumes difficult is the fact that small residual liquid volumes do not readily absorb light rays. A second reason is that the containers (mostly glass bottles) in which the liquid is filled, also absorb, to a certain extent, the light rays which pass through them. It is often the case that the light rays received on the photoelectric transducer sensor varies depending upon the container wall thickness as well as the applied color of the container.

In order to detect very small volumes of the residual liquid, it is necessary to amplify and magnify the subtle variations in the output voltage from the photoelectric transducer. Such amplified magnification of the variation at the same time magnifies variations due to the passage of transient light through the container walls, and accordingly it becomes difficult to detect the true variation of the received light by the actual residual liquid. Therefore, there is a limit to the accuracy in the detection of very small volumes of residual liquid, and it is the present practice to accept such detection when the residual liquid is over a certain predetermined volume.

OBJECTS AND SUMMARY OF THE INVENTION

It is an object of the present invention to provide a residual liquid detection apparatus free from the defects encountered in the prior art.

It is another object of the present invention to provide a residual liquid detection apparatus which can detect a small amount of residual remaining in the bottom of a transparent bottle.

It is a further object of the present invention to provide a residual liquid detection apparatus which can detect a small amount of residual liquid in the bottom of a transparent bottle regardless of the thickness of the bottle, its color, or the like.

According to a first aspect of the present invention, there is provided a residual liquid detection apparatus for detecting whether or not liquid remains at the bottle bottom of a transparent bottle, which comprises:

a) a light source for irradiating a light that contains visible light rays and infrared rays onto the bottle bottom of the bottle;

b) two photoelectric conversion sensors for receiving light that has passed through said bottle bottom from said light source;

c) an optical filter which only passes the infrared rays placed in front of the light receiving surface of one of said photoelectric conversion sensors; and d) circuit means for comparing the outputs of two photoelectric conversion sensors and delivering a signal when a difference between the output exceeds a predetermined value.

According to a second aspect of the present invention, there is provided a residual liquid detection apparatus for detecting whether or not liquid remains at the bottle bottom of a transparent bottle, which comprises:

a) a light source located under the bottom of a transparent bottle for irradiating light that contains visible light rays and infrared rays onto the bottle bottom;

b) a light diffusing plate located between said light source and said bottle bottom;

c) two photoelectric conversion sensors located above the bottle mouth of said transparent bottle and for receiving light that has passed through said bottle bottom from said light source;

d) a condenser lens located between said two photoelectric conversion sensors and said bottle mouth;

e) an optical filter which only passes the infrared rays and is placed in front of the light receiving surface of one of said photoelectric conversion sensors; and f) circuit means for comparing outputs from said two photoelectric conversion sensors and delivering a signal when a difference between the outputs exceeds a predetermined value.

According to a third aspect of the present invention, there is provided a residual liquid detection apparatus for detecting whether or not liquid remains at the bottle bottom of a transparent bottle, which comprises:

a) a light source located under the bottle bottom of a transparent bottle for irradiating light that contains visible light rays and infrared rays onto the bottle bottom;

b) a light diffusing plate located between said light source and said bottle bottom;

c) two photoelectric conversion sensors located above the bottle mouth of said transparent bottle for receiving light that has passed through said bottle bottom from said light source;

d) a condenser lens located between said two photoelectric conversion sensors and said bottle mouth;

e) an optical filter which only passes the infrared rays and is placed in front of the light receiving surface of one of said photoelectric conversion sensors;

f) a light splitter located between said condenser lens and said two photoelectric conversion sensors; and g) a circuit for comparing outputs from said two photoelectric conversion sensors and delivering a signal when a difference between the outputs exceeds predetermined value, wherein the optical axis of said condenser lens is made coincident to the center axis of said bottle, the other photoelectric conversion sensor having no optical filter is located to receiver the light propagated along said optical axis and passing through said light splitter, and the other photoelectric conversion sensor is located to receive the light which is propagated along said optical axis and is reflected by said light splitter.

According to a fourth aspect of the present invention, there is provided a residual liquid detection apparatus for detecting whether or not liquid remains at the bottle bottom of a transparent bottle, which comprises:

a) a light source located under the bottle bottom of the transparent bottle for irradiating light that contains visible light rays and infrared rays onto the bottle bottom;

b) a light diffusing plate located between said light source and said bottle bottom;

c) two photoelectric conversion sensors located above the bottle mouth of said transparent bottle for receiving light that has passed through said bottle bottom from said light source;

d) a condenser lens located between said two photoelectric conversion sensors and said bottle mouth;

e) an optical filter which only passes the infrared rays placed in front of the light receiving surface of one of said photoelectric conversion sensors; and f) circuit means for comparing the outputs from said two photoelectric conversion sensors and delivering a signal when a difference between the outputs exceeds a predetermined value, wherein the optical axis of said condenser lens is coincident to the center axis of said bottle, said two photoelectric conversion sensors being concentrically located with respect to said optical axis in the same plane.

The above and other objects, features, and advantages of the present invention will become apparent from the following detailed description taken in conjunction with the accompanying drawings through which like reference numerals designate the same and similar elements.

DETAILED DESCRIPTION OF THE PREFERRED EMBODIMENTS

Figure 1:
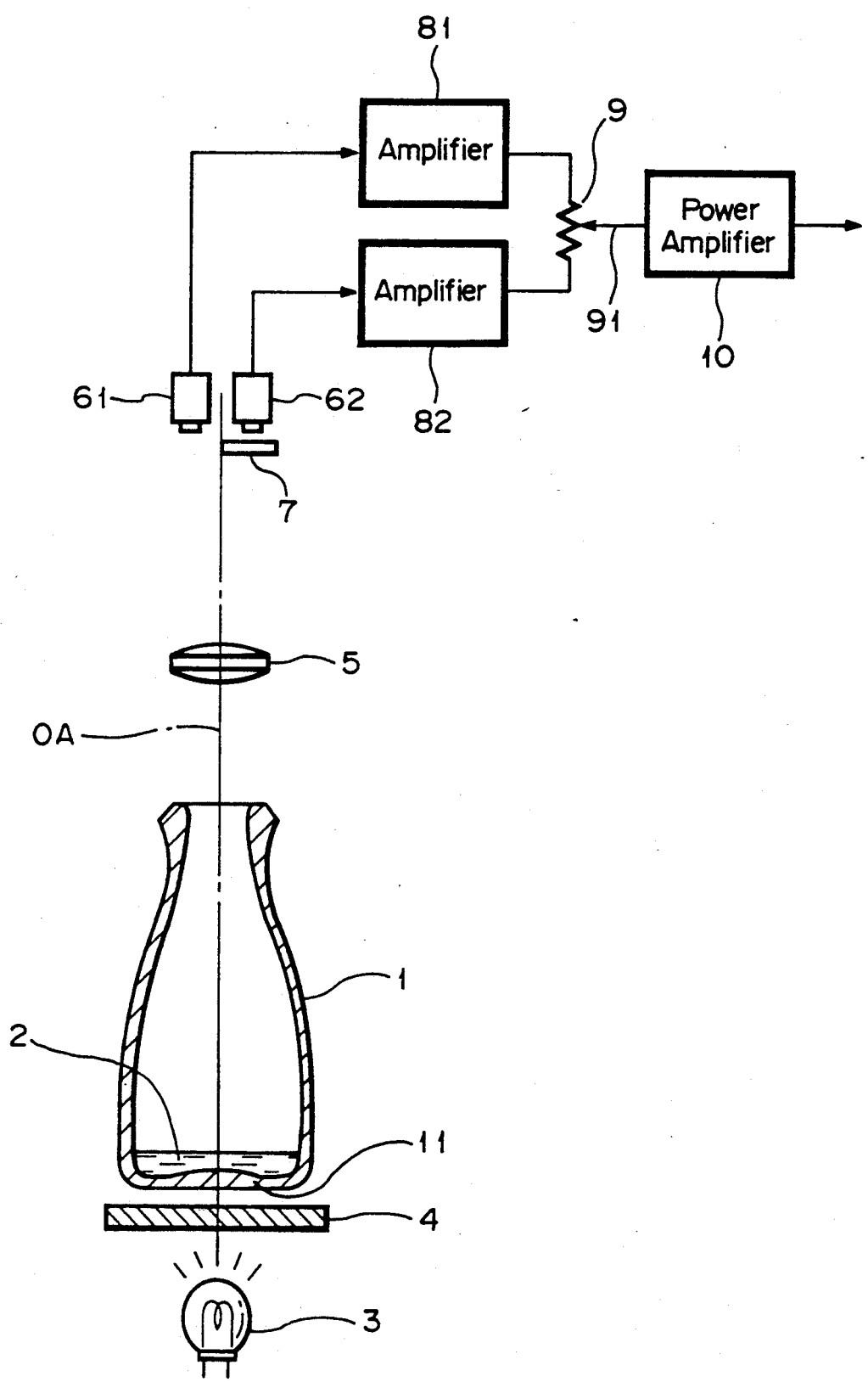
FIG. 1 is a schematic diagram showing an embodiment of the present invention.

In FIG. 1, a glass bottle 1 or the like containing residual liquid 2 at the bottom 11. A light source 3 is located beneath the bottle bottom 11 radiating light that includes visible light rays as well as infrared rays on the bottom 11 of the bottle 1. A light diffusion plate 4 is placed between the bottle bottom 11 and the light source 3 in order to cause an even irradiation of the light onto the bottle bottom 11. A condenser lens 5 is placed above the bottle mouth in order to converge the light that has passed through he bottle bottom 11. The optical axis OA of the condenser lens 5 is arranged to match the center axis of the bottle 1 as indicated. Two photoelectric conversion sensors 61, 62 are placed above the condenser lens 5 in a parallel manner to each other to straddle the optical axis OA. An optical filter 7 that only passes infrared rays is located in front of the light receiving face of one photoelectric conversion sensor 62. Two amplifiers 81, 82 respectively boost the photoelectric converted outputs from photoelectric conversions 61, 62. A zero adjuster 9 such as a potentiometer adjusts and nulls the voltage differences between the two amplifiers 81, 82. A power amplifier 10 is connected to an intermediate tap 91 of the zero adjuster 9 in order to generate a detection output signal.

Photoelectric conversion sensors 61, 62 are located close to each other so that the optical image of bottle bottom 11, which is formed by focussing the light passing through the bottle bottom 11 by means of condenser lens 5, occupies both photoelectric conversion sensors 61, 62 by similar areas (which will be described later in connection with FIG. 2). The electrical outputs from photoelectric conversion sensors (transducers) 61, 62 are respectively amplified by amplifiers 81, 82 and supplied to the zero adjuster 9. If a positive phase amplifier is used as one amplifier 81, while a negative phase amplifier is used as the other amplifier 82 and the outputs from both amplifiers 81, 82 are supplied to the zero adjuster 9, the voltages at the both ends of the zero adjuster 9 (potentiometer) will be reversed in phase to each other. Therefore, when there is no residual liquid 2 exists at bottle bottom 11, both photoelectric conversion sensors 61, 62 and so on are adjusted to make the voltage at intermediate tap 91 zero. Then, when the irradiated light is received by the sensors 61, 62 and there is no residual liquid 2 at bottle bottom 11, if there is a slight voltage difference at the intermediate tap 91, the potentiometer 9 can be adjusted to make the voltage difference at its intermediate tap 91 be zero.

A light source which emits both visible light rays as well as infrared rays is used as the light source 3. One photoelectric conversion sensor 61 receives the actual light as its passes through the bottle bottom 11 as well as the residual liquid 2 at bottle bottom 11. On the other hand, since there is the optical filter 7, which allows only the infrared rays to pass, placed in front of the light receiving surface of the other photoelectric conversion sensor 62, it only receives the infrared rays of the light source.

Generally speaking, in the case of infrared rays having long wave length in the range of 1 to 2 microns, the attenuation coefficient of infrared rays passing through the liquid becomes extremely large. Accordingly, when there is residual liquid 2 at the bottle bottom 11 the photoelectric converted output, from the photoelectric conversion sensor 62 that only receives the infrared rays, becomes extremely small as compared with that from the other photoelectric conversion sensor 61. As for the optical filter 7, any proper type that has a cutoff frequency range of the above-mentioned range (within the infrared range) will suffice.

Photoelectric conversion sensor 61 also receives the light in the visual zone, when passing through the liquid, is small so that the amount of light received by photoelectric conversion sensor 61 does not show large variations whether or not residual liquid exists in the bottle. For the above reason, the existence or not of residual liquid 2 will generate a large difference between the electrical output from the amplifier 81 that is connected to photoelectric conversion sensor 61 and the amplifier 82 that is connected to photoelectric conversion sensor 62. Therefore, if the zero adjuster 9 is so adjusted that the voltage difference at its output terminal 91 connected to amplifiers 81, 82 is nil, when there is no residual liquid 2 at the bottle bottom 11. A voltage difference will appear at the output terminal 91 only when there is residual liquid 2 existing on the bottom 11 of bottle 1.

The output from the zero adjuster 9 is supplied to the power amplifier 10. This power amplifier 10 is adjusted to generate an electrical output that indicates the detection of residual liquid 2 at the bottle bottom 11 when the voltage from the zero adjuster 9 exceeds a predetermined constant value. Needless to say, by utilizing the electrical output from the power amplifier 10, although not shown on FIG. 1, alarm means either light or sound may be driven, or a bottle rejection system may be activated to remove the bottles having residual liquid 2.

Figure 2:
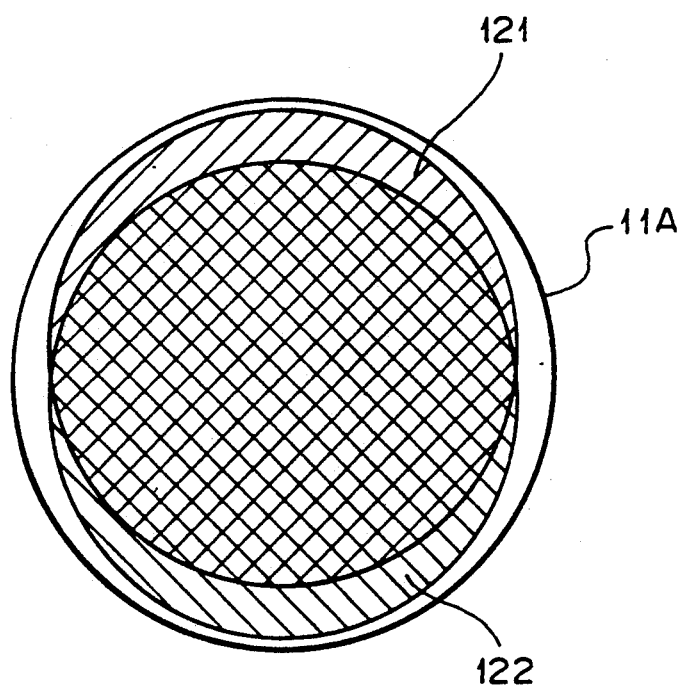
FIG. 2 is a schematic diagram that is used to explain the functions of the same.

FIG. 2 is a plane diagram that shows magnified light receiving areas of photoelectric conversion sensors 61 and 62, respectively. In FIG. 2, 11A is an inner diameter area of bottle bottom 11, and 121, 122 are the light received areas of the photoelectric conversion sensors 61, 62 corresponding to the inner diameter area 11A. The two photoelectric conversion sensors 61, 62 are installed close together, and are only slightly displaced from the optical axis OA of the condenser lens 6 so that there will be a slight difference between the light received areas 121, 122. Although there is a slight difference in the light receiving areas, from the purpose of residual liquid 2 detection, this, in fact, does not create any problem because of the wider overlap. Even when the photoelectric conversion sensors 61, 62 are set up so that the light from different portions of the bottle bottom 11 are received by the photoelectric sensors 61, 62, respectively, it is apparent that the purpose of the present invention can be accomplished according to the functional principles of the present invention.

Figure 3:
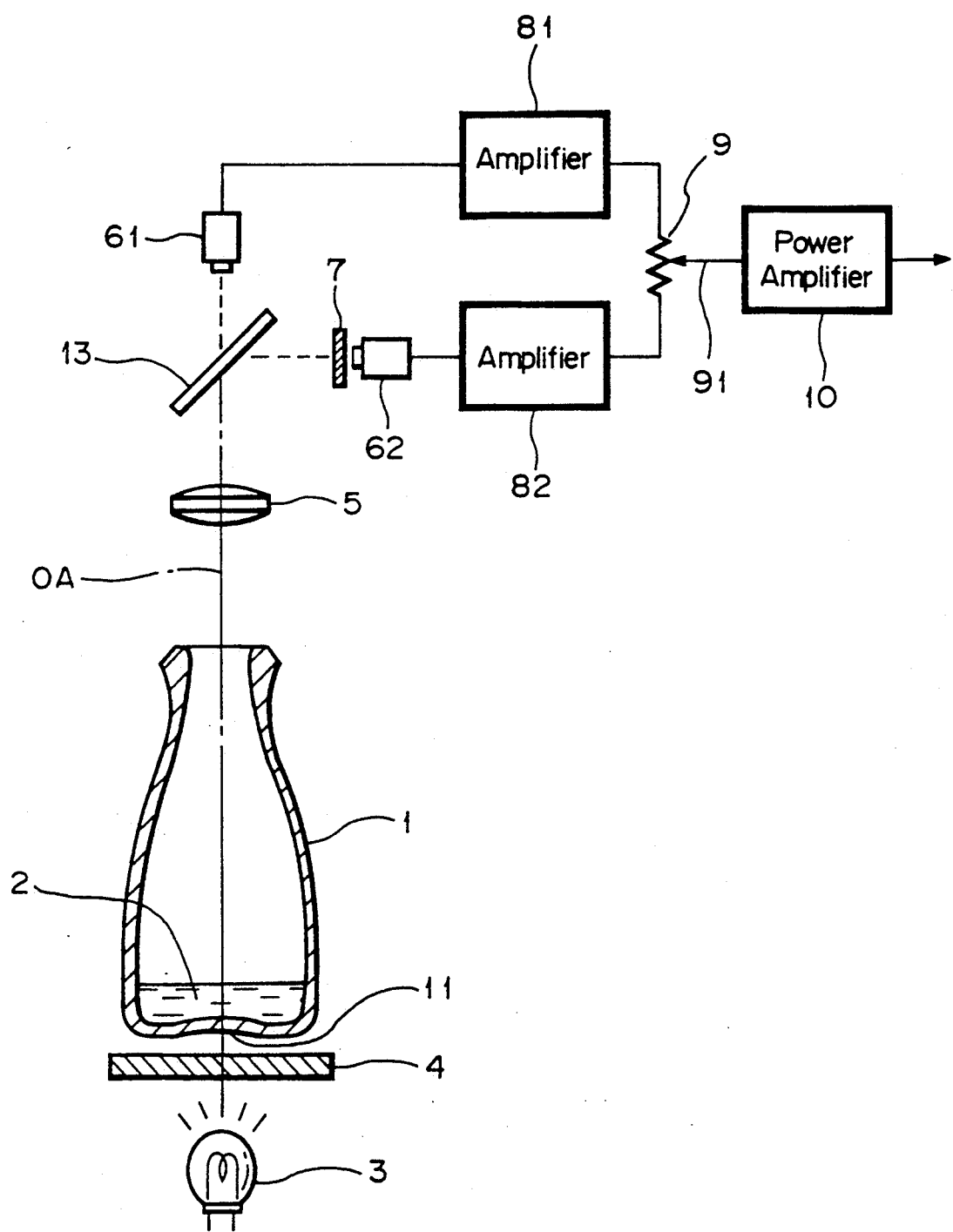
FIG. 3 is a block diagram showing a second embodiment of the present invention.

FIG. 3 shows a second embodiment of the present invention where the described difference in the light receiving areas of photoelectric conversion sensors 61, 62 will not occur. In other words, as shown in FIG. 3, a light splitter 13 such as a half mirror, a prism or the like is placed in the optical axis OA between the condenser lens 5 and the photoelectric conversion sensors 61, 62 so that one photoelectric conversion sensor 61 will receive the light that has passed through the bottle bottom 11, while the other photoelectric conversion sensor 62 will receive the light refracted by the splitter 13. By such arrangement, the light receiving areas of photoelectric conversion sensors 61, 62 can be made to match. The other parts of the second embodiment will be exactly the same to those of the embodiment of FIG. 1.

Figure 4A:
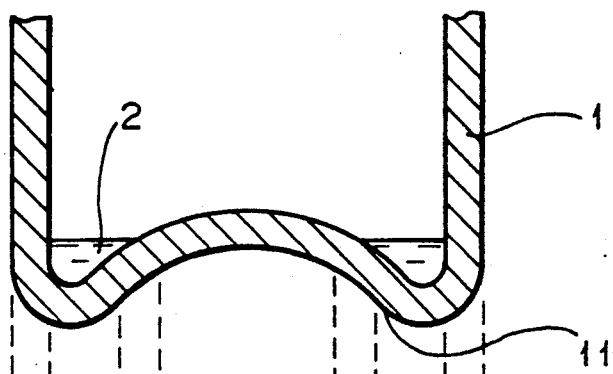
FIGS. 4A and 4B are schematic diagrams used to explain a third embodiment of the present invention.
Figure 4B:
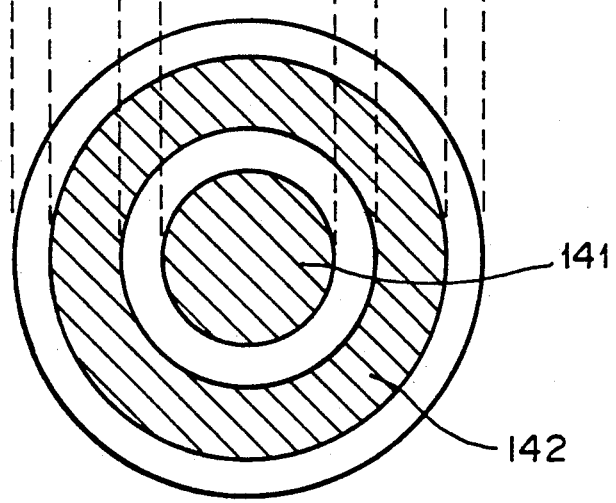
Figure 5:
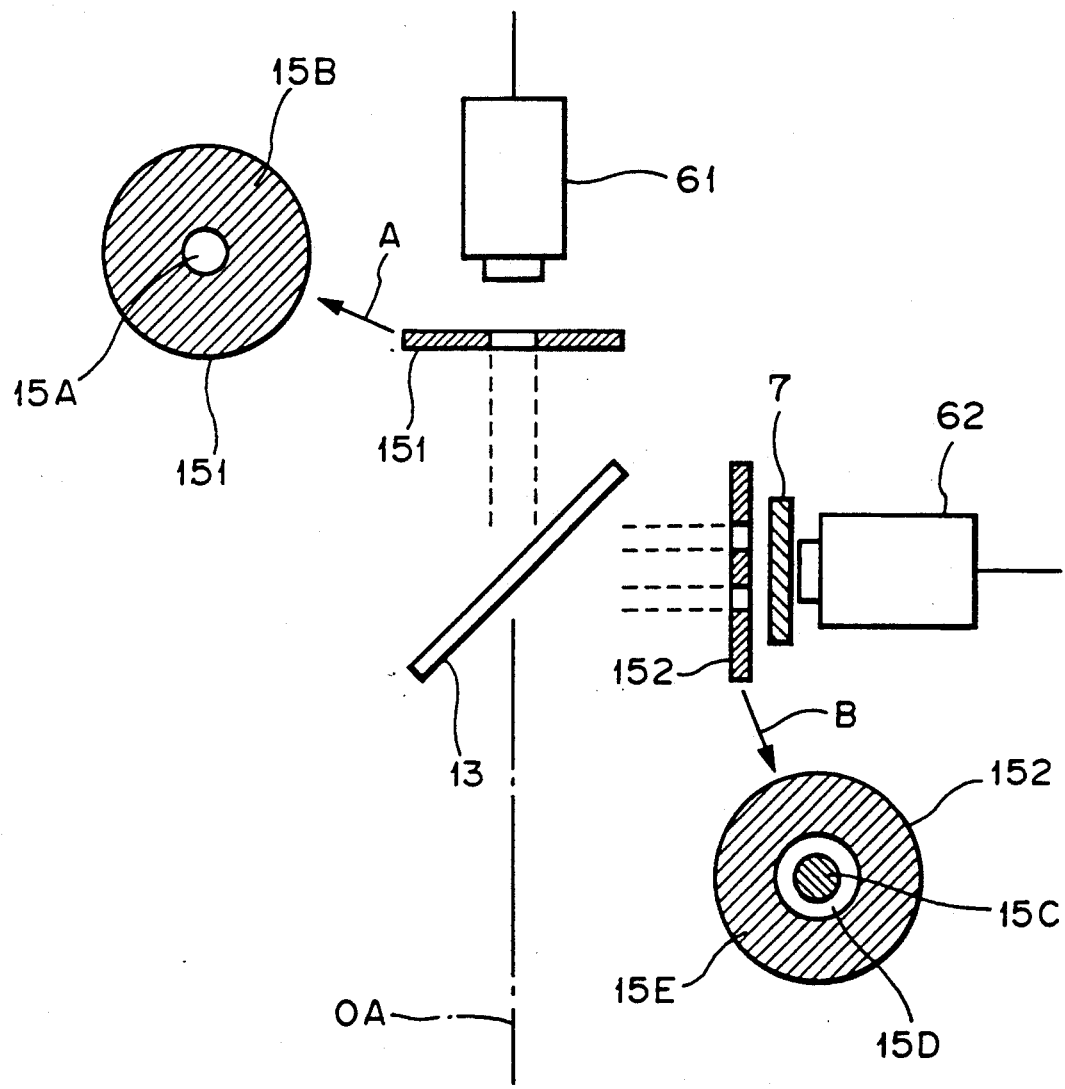
FIG. 5 is a schematic diagram showing a main part of the third embodiment of the present invention.

FIG. 4 and FIG. 5 are schematic diagrams showing the main part of a third embodiment of the present invention, where a bottle 1 is shown having a central portion at the bottom 11 which protrudes upwards as shown in the sectional side view FIG. 4A. In this case, when the amount of the residual liquid 2 is small, such residual liquid 2 will be spread in a doughnut like shape at the outer circumferential area of the bottle bottom 11 and will not exist at the center or protruded portion of the bottom 11.

In order to effectively detect the existence of any residual liquid 2 in such a bottle, the third embodiment of the present invention as seen in reference to FIG. 4B and FIG. 5. As shown on one photoelectric conversion sensor 61 will receive only the light that passes through the central protruded portion 141 of bottle bottom 11 (along axis OA), while the other photoelectric conversion sensor 62 will receive only the light that passes through the doughnut like portion 142 around the center of the bottle bottom 11. By such arrangement, the photoelectric conversion sensor 62 will be affected by the attenuation degree of the passed light dependent on the residual liquid 2 in the doughnut 142, so that an effective detection of a small amount of residual liquid 2 is possible.

Figure 6:
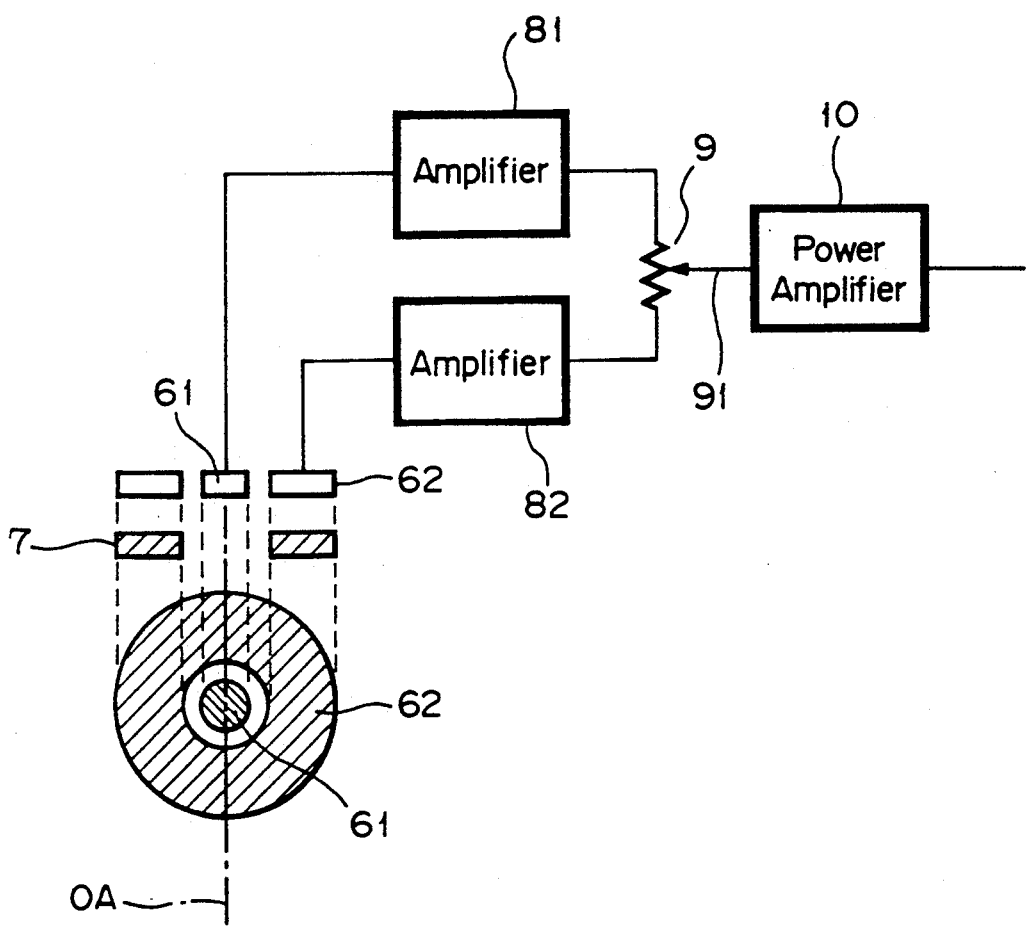
FIG. 6 is a block diagram showing a fourth embodiment of the present invention.

As shown on FIG. 5, an optical mask 151 is placed in front of the light receiving surface of photoelectric conversion sensor 61 and an optical mask 152 is placed in front of the light receiving surface of photoelectric conversion sensor 62. As shown on the left offset plane diagram indicated by arrow A, the optical mask 151 is formed of a disc-shaped transparent portion 15A at the center thereof and an opaque portion 15B surrounding the same. The other optical mask 152, as shown in the downwardly offset plane diagram B is formed of a disc-shaped opaque central circular portion 15C, a doughnut-shaped transparent portion 15D surrounding the same and another ring-shaped opaque section 15E surrounding the portion 15D. Therefore, the respective optical masks 151 and 152 are limited to the light receiving areas corresponding to the portions 141, 142 as seen in FIG. 4B. Even if the optical mask 151 is omitted and the entire light passing through the bottle bottom 11 is received by the photoelectric conversion sensor 61, there is no obstacle to the function of the present invention as seen in FIG. 5. Also although not shown on FIG. 5, the other structure and functions of this embodiment are exactly the same as those of the embodiment of the present invention where the structures of the photoelectric conversion sensors 61, 62 are special formed so that without the use of the half mirror or splitter 13, the light passed through bottle bottom 11 is received by the photoelectric sensors 61, 62 along the optical axis OA. In other words, the photoelectric conversion sensor 61 is shaped as a small disc while the photoelectric conversion sensor 62 is shaped as a doughnut and placed to surround the smaller disk as shown in FIG. 6. Both the photoelectric conversion sensors 61, 62 are placed on the same plane and concentric to the optical axis OA. By this arrangement, the photoelectric conversion sensor 61 will only receive the light passing through the center portion of the bottle bottom 11 while photoelectric conversion sensor 62 will receive the light passing only through the outer circumference doughnut-shaped portion of the bottle bottom 11 Thus, this in effect provides the same function to that of the embodiment of FIG. 5. It is needless to say that it will be necessary to install the same doughnut-shaped infrared ray filter 7 in front of the light receiving surface of photoelectric conversion sensor 62.

While the foregoing embodiments of the present invention refer to a structured arrangement where the bottle bottom 11 is irradiated from beneath the bottom 11 and the light passing through the bottom 11 is received above the bottle mouth, however, in order to practice the present invention, it is not necessary to be limited to this arrangement and many other constructions may be considered.

Figure 7A:
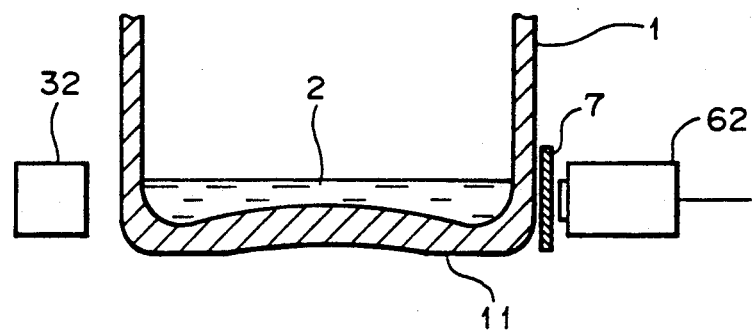
FIGS. 7A and 7B are schematic diagrams showing a main part of a fifth embodiment of the present invention.
Figure 7B:
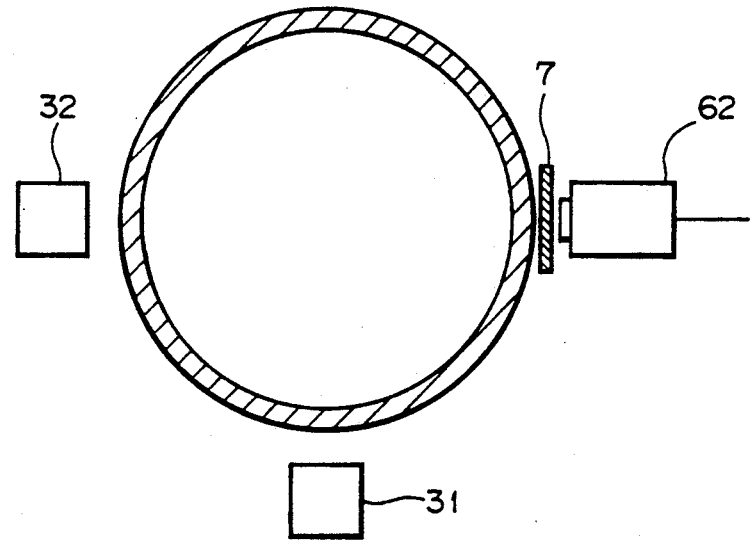

For example, in FIGS. 7A and 7B, a fifth embodiment of the present invention is shown where the photoelectric conversion sensors 61 and 62 are placed at perpendicular radii at the outside of the bottle 1 near the bottle bottom 11. In this case, the light source 3 is formed by two projection type light sources 31, 32 placed outside the bottle bottom 11, in opposing positions to the photoelectric conversion sensors 61, 62. The locations of the light sources 31 and 32 will be arranged so that such respective light beams shall pass the residual liquid 2 and be received by the photoelectric conversion sensors 61, 62, respectively, in order that the detection of the residual liquid 2 will be effective. The other structures and functions of this embodiment are the same to those of the previously explained embodiments and such drawings and explanations shall not be cited.

Further, in the foregoing embodiments conventional cases of convenient photoelectric conversion sensors are used. However, with the use of video cameras and CPU or the like, it will be easy for anyone skilled in the art to enable commencement of the main functions and effects of the present invention by computer logic.

According to the present invention, the prior difficulty in detecting small amounts of residual liquid is overcome with the additional benefit of removing the impediment to improved detection, precision and stability which might otherwise have been caused by the container (glass bottles or the like) thickness or variations in the colour.

It should be understood that the above description is presented by way of example on the preferred embodiments of the invention and it will be apparent that many modifications and variations thereof could be effected by one with ordinary skill in the art without departing from the spirit and scope of the novel concepts of the invention so that the scope of the invention should be determined only by the appended claims.

I claim as my invention:

1. A residual liquid detection apparatus for detecting whether or not liquid remains at the bottle bottom of a transparent bottle, comprising:
   a) a light source for irradiating light that contains visible light rays and infrared rays onto the bottom of the bottle;
   b) two photoelectric conversion sensors for receiving the light passing through said bottle bottom from said light source;
   c) a single optical filter which passes only the infrared rays placed in front of the light receiving surface of one of said photoelectric conversion sensors wherein the other of said photoelectric conversion sensors detects both visible light and IR rays from said light source; and
   d) means for directly comparing the outputs from said two photoelectric conversion sensors and providing a signal when a difference between the outputs exceeds a predetermined value.

2. A residual liquid detection apparatus for detecting whether or not liquid remains at the bottle bottom of a transparent bottle, comprising:
   a) a light source located beneath the bottle bottom for irradiating said bottle bottom with light that contains visible light rays and infrared rays;
   b) a light diffusing plate located between said light source and said bottle bottom;
   c) two photoelectric conversion sensors located above the bottle mouth of said transparent bottle for receiving light passing through said bottle bottom from said light source;
   d) a lens located between said two photoelectric conversion sensors and said bottle mouth for condensing light passing to said sensors;
   e) a single optical filter which passes only the infrared rays placed in front of the light receiving surface of one of said photoelectric conversion sensors wherein the other of said photoelectric conversion sensors detects both visible light and IR rays from said light source; and
   f) means for directly comparing the outputs from said two photoelectric conversion sensors and providing a signal when a difference between the outputs exceeds a predetermined value.

3. A residual liquid detection apparatus for detecting whether or not liquid remains at the bottle bottom of a transparent bottle, comprising:
   a) a light source located beneath the bottle bottom of a transparent bottle for irradiating the bottle bottom with light that contains visible light rays and infrared rays;
   b) a light diffusing plate located between said light source and said bottle bottom;
   c) two photoelectric conversion sensors located above the bottle mouth of said transparent bottle for receiving the light passing through said bottle bottom from said light source;
   d) a lens located between said two photoelectric conversion sensors and said bottle mouth for condensing the light passing to said sensors;
   e) a single optical filter which passes only the infrared rays placed in front of the light receiving surface of one of said photoelectric conversion sensors wherein the other of said photoelectric conversion sensors detects both visible light and is IR rays from said light source;
   f) means located between said condenser lens and said two photoelectric sensors for splitting said light and passing said light to said sensors respectively; and
   g) means for directly comparing the outputs from said two photoelectric conversion sensors and providing a signal when a the difference between the outputs exceeds a predetermined value, the optical axis of said condenser lens being made coincident to the center axis of said bottle, said photoelectric conversion sensor having no optical filter being located to receive the light which propagates along said optical axis and passes through said light splitter, and the other photoelectric conversion sensor being located to receive the light which propagates along said optical axis and is reflected by said light splitter.

4. A residual liquid detection apparatus for detecting whether or not liquid remains at the bottle bottom of a transparent bottle as claimed in claim 3, wherein said light splitter means is a half mirror.

5. A residual liquid detection apparatus for detecting whether or not liquid remains at the bottle bottom of a transparent bottle as claimed in claim 3, wherein said light splitter means is a prism.

6. A residual liquid detection apparatus for detecting whether or not liquid remains at the bottle bottom of a transparent bottle according to claim 3 including:
two optical masks located respectively in front of the light receiving surfaces of each of said two photoelectric conversion sensors.

7. A residual liquid detection apparatus for detecting whether or not liquid remains at the bottle bottom of a transparent bottle as claimed in claim 6, wherein one of said two optical masks is formed with a disc-shaped transparent central portion and an opaque portion surrounding said disc-shaped transparent portion, while the other of said two optical mask is formed with a disc-shaped opaque central portion, a doughnut-shaped transparent portion surrounding said disc-shaped portion and a ring-shaped opaque portion surrounding said transparent portion.

8. A residual liquid detection apparatus for detecting whether or not liquid remains at the bottle bottom of a transparent bottle, comprising:
a) a light source located beneath the bottle bottom of a transparent bottle for irradiating the bottle bottom with light that contains visible light rays and infrared rays;
b) a light diffusing plate located between said light source and said bottle bottom;
c) two photoelectric conversion sensors located above the bottle mouth of said transparent bottle for receiving the light passing through said bottle bottom from said light source;
d) a lens located between said two photoelectric conversion sensors and said bottle mouth for condensing the light passing to said sensors;
e) an optical filter which passes only the infrared rays placed in front of the light receiving surface of one of said photoelectric conversion sensors wherein the other of said photoelectric conversion sensors detects both visible light and IR rays from said light source; and
f) means for directly comparing the outputs from said two photoelectric conversion sensors and providing a signal when a difference between the outputs exceeds a predetermined value, the optical axis of said condenser lens being made coincident to the center axis of said bottle, and said two photoelectric conversion sensors are concentrically located with respect to said optical axis co-planar with each other.

9. A residual liquid detection apparatus for detecting whether or not liquid remains at the bottle bottom of a transparent bottle as claimed in claim 8, wherein one of said two photoelectric conversion sensors is disc shaped while the other photoelectric conversion sensor is doughnut shaped concentrically surrounding the former and spaced therefrom.

* * * * *